United States Patent
Knappe et al.

(10) Patent No.: US 10,675,235 B2
(45) Date of Patent: Jun. 9, 2020

(54) ACTIVE AGENT MIXTURES FOR STYLING PRODUCTS

(71) Applicant: Henkel AG & Co. KGaA, Dusseldorf (DE)

(72) Inventors: Thorsten Knappe, Schenefeld (DE); Anja Thammasiri, Klein Nordende (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 15/665,429

(22) Filed: Aug. 1, 2017

(65) Prior Publication Data

US 2018/0098929 A1    Apr. 12, 2018

(30) Foreign Application Priority Data

Oct. 12, 2016   (DE) .................. 10 2016 219 843

(51) Int. Cl.
*A61K 8/81*    (2006.01)
*A61K 8/04*    (2006.01)
*A61Q 5/06*    (2006.01)

(52) U.S. Cl.
CPC .............. *A61K 8/817* (2013.01); *A61K 8/046* (2013.01); *A61K 8/8158* (2013.01); *A61K 8/8182* (2013.01); *A61Q 5/06* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,997,883 A | 12/1999 | Epstein et al. | |
| 6,149,898 A | 11/2000 | Peffly et al. | |
| 2003/0198603 A1* | 10/2003 | Rollat-Corvol | A61K 8/046 424/47 |
| 2010/0008885 A1* | 1/2010 | Daly | A61K 8/463 424/70.27 |
| 2010/0186764 A1* | 7/2010 | Pasquet | A61K 8/8147 132/203 |
| 2010/0266794 A1* | 10/2010 | Wright | A61L 15/60 428/35.7 |
| 2011/0104090 A1 | 5/2011 | Kelton et al. | |
| 2011/0110878 A1 | 5/2011 | Knappe et al. | |
| 2015/0017113 A1 | 1/2015 | Metten et al. | |
| 2015/0110729 A1 | 4/2015 | Metten et al. | |

FOREIGN PATENT DOCUMENTS

DE      102014221400 A1    4/2016

OTHER PUBLICATIONS

Intellectual Property Office, Search Report under Section 17(5) for United Kingdom Patent Application No. GB1714847.9 dated Jun. 1, 2018.

* cited by examiner

*Primary Examiner* — David J Blanchard
*Assistant Examiner* — Sarah J Chickos
(74) *Attorney, Agent, or Firm* — Lorenz & Kopf, LLP

(57) ABSTRACT

A cosmetic product for temporarily reshaping keratin-containing fibers, in particular human hair, containing, in a cosmetic carrier, in relation to its total weight,
a) from about 0.01 to about 10 wt. % of at least one (meth)acrylamidopropyltrimethylammonium salt homo- or copolymer;
b) from about 0.1 to about 10 wt. % of at least one non-ionic, anionic and/or amphoteric film-forming polymer,
use thereof, and method using this product.

20 Claims, No Drawings

ACTIVE AGENT MIXTURES FOR STYLING PRODUCTS

CROSS-REFERENCE TO RELATED APPLICATION

This application claims priority to German Patent Application No. 10 2016 219 843.2, filed Oct. 12, 2016, which is incorporated herein by reference in its entirety.

TECHNICAL FIELD

The present disclosure relates to cosmetic products for temporarily reshaping keratin-containing fibers which contain, in a cosmetic carrier, a combination of at least one (meth)acrylamidopropyltrimethylammonium salt homo- or copolymer and at least one non-ionic, anionic and/or amphoteric film-forming polymer.

BACKGROUND

The present disclosure also relates to methods for temporarily reshaping keratin-containing fibers and to the use of the cosmetic products to improve the hair volume, manageability, styling hold, and to prevent and reduce hair damage, in particular hair breakage.

Products for temporary shaping are known per se. They usually contain synthetic polymers as shaping components. Preparations that contain a dissolved or dispersed polymer can be applied to the hair by employing propellant gases or by a pump mechanism. Hair gels and hair waxes in particular, however, generally are not applied directly to the hair, and instead are distributed through the hair by employing a comb or by hand.

The most important property of a product for temporarily shaping keratin-containing fibers, referred to hereinafter as styling products, lies in providing the treated fibers in the created form with the strongest possible hold. If the keratin-containing fibers are human hair, reference is also made to a strong hairstyle hold or to a high holding power of the styling product. Apart from the hairstyle hold, further customer requirements relate to the hair volume achieved, the manageability, and the nourishment of the hair.

Cosmetic styling products generally contain individual polymers which are specially tailored to the objective of attaining a rather specific effect. If various effects are to be attained, the addition of a plurality of polymers is necessary. If, however, too many different polymers are used, this can result in a series of disadvantages. Problems may arise in the formulation, for example because the polymers react with one another or with other constituents of the product, thus resulting in precipitations or breakdown. Certain polymers also tend to become deposited so firmly on the skin and in particular on the hair that they can no longer be fully removed during the course of habitual washing, thus resulting in an undesirable build-up of the polymer, which ultimately loads the skin or hair.

There is thus an on-going need for polymers or suitable combinations of a small number of polymers simultaneously having as many of the desired properties as possible.

By way of example, it is necessary in the case of styling products that the used polymers provide the treated hair with the strongest hold possible. Besides a high holding power, styling products must also satisfy a wide range of further requirements. These can be divided roughly into properties on the hair, properties of the formulation in question, for example properties of the mousse, the gel, or the sprayed aerosol, and properties that concern the handling of the styling product, wherein the properties on the hair are attributed particular importance. In particular, moisture resistance, low stickiness, and a balanced conditioning effect can be cited. Furthermore, a styling product should be universally usable for all hair types where possible and should give the hair volume and fullness.

BRIEF SUMMARY

Cosmetic products and methods for shaping keratin containing-fibers are provided. In an exemplary embodiment, a cosmetic product includes, in a cosmetic carrier, in relation to the cosmetic product's total weight, from about 0.01 to about 10 weight percent of at least one (meth) acrylamidoproplytrimethylammonium salt homo- or copolymer a). The cosmetic product also includes, in relation to the cosmetic product's total weight, from about 0.1 to about 10 weight percent of at least one non-ionic, anionic, and/or amphoteric film-forming polymer b).

A method of shaping keratin-containing fibers is provided in another embodiment. The method includes applying a cosmetic product to the keratin-containing fibers, where the cosmetic product includes, in a cosmetic carrier, in relation to the total weight of the cosmetic product, from about 0.01 to about 10 weight percent of at least one (meth)acrylamidoproplytrimethylammonium salt homo- or copolymer a). The cosmetic product also includes, in relation to the total weight of the cosmetic product, from about 0.1 to about 10 weight percent of at least one non-ionic, anionic, and/or amphoteric film-forming polymer b).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide products for temporarily shaping keratin-containing fibers which enable a significant improvement of the hairstyle hold and the feel of the hair (soft feel and elasticity). The object of the present disclosure was in particular to provide products that improve the fullness of the hair and the volume of the hair and also the manageability of the hair. Damage to the hair, in particular hair breakage, should also be reduced.

These objects were achieved by a specific active agent combination, comprising a (meth)acrylamidopropyltrimethylammonium salt homo- or copolymer and at least one non-ionic, anionic and/or amphoteric film-forming polymer. Haircare products based on (meth)acrylamidopropyltrimethylammonium salt homopolymer are described for example in German patent application DE 10 2014 221 400 A1.

The products and methods as contemplated herein and some of the preferred embodiments thereof are exemplified by the following points:

1. A cosmetic product for temporarily reshaping keratin-containing fibers, in particular human hair, containing, in a cosmetic carrier, in relation to its total weight,
a) from about 0.01 to about 10 wt. % of at least one (meth)acrylamidopropyltrimethylammonium salt homo- or copolymer;
b) from about 0.1 to about 10 wt. % of at least one non-ionic, anionic and/or amphoteric film-forming polymer.

2. The cosmetic product according to point 1, exemplified in that it contains, as (meth)acrylamidopropyltrimethylammonium salt homo- or copolymer, a) a (meth)acrylamidopropyltrimethylammonium salt homopolymer, preferably (3-acrylamidopropyl)trimethylammonium salt homopolymer, preferably (3-acrylamidopropyl)trimethylammonium chloride homopolymer.

3. The cosmetic product according to point 1, exemplified in that it contains, as (meth)acrylamidopropyltrimethylammonium salt homo- or copolymer, a) a (meth)acrylamidopropyltrimethylammonium salt homopolymer, preferably (3-methacrylamidopropyl)trimethylammonium salt homopolymer, preferably (3-methacrylamidopropyl)trimethylammonium chloride homopolymer.

4. The cosmetic product according to any one of the preceding points, exemplified in that the proportion by weight of the (meth)acrylamidopropyltrimethylammonium salt homo- or copolymer a), preferably of the (meth)acrylamidopropyltrimethylammonium salt homopolymer a), in the total weight of the cosmetic product is from about 0.02 to about 8.0 wt. %, preferably from about 0.05 to about 6.0 wt. %, and in particular from about 0.1 to about 3.0 wt. %.

5. The cosmetic product according to any one of the preceding points, exemplified in that the film-forming polymer b) is selected from the group of non-ionic polymers.

6. The cosmetic product according to any one of the preceding points, exemplified in that the film-forming polymer b) is selected from the group of vinylpyrrolidone homopolymers.

7. The cosmetic product according to any one of the preceding points, exemplified in that the film-forming polymer b) is selected from the group of vinyl acetate/vinylpyrrolidone copolymers.

8. The cosmetic product according to any one of the preceding points, exemplified in that the film-forming polymer b) is selected from mixtures of vinylpyrrolidone homopolymer and vinyl acetate/vinylpyrrolidone copolymer.

9. The cosmetic product according to any one of the preceding points, exemplified in that the proportion by weight of the film-forming polymer b) in the total weight of the cosmetic product is from about 0.2 to about 9.0 wt. %, preferably from about 0.25 to about 8.0 wt. %, and in particular from about 0.3 to about 7.0 wt. %.

10. The cosmetic product according to any one of the preceding points, exemplified in that the product also contains, in relation to its total weight, from about 0.1 to about 6.0 wt. %, preferably from about 0.2 to about 5.0 wt. %, preferably from about 0.3 to about 4.0 wt. %, and in particular from about 0.4 to about 3.0 wt. % of at least one cationic nourishing active agent different from the (meth)acrylamidopropyltrimethylammonium salt homopolymer.

11. The cosmetic product according to point 10, exemplified in that the cationic nourishing active agent is selected from the group of cationic surfactants.

12. The cosmetic product according to point 10, exemplified in that the cationic nourishing active agent is selected from the group of cationic polymers.

13. The cosmetic product according to any one of the preceding points, exemplified in that the product also contains, in relation to its total weight, from about 0.05 to about 2.0 wt. %, preferably from about 0.1 to about 1.0 wt. %, and in particular from about 0.1 to about 0.5 wt. % of at least one non-ionic surfactant from the group of addition products of from about 30 to about 60 mol ethylene oxide with castor oil and hardened castor oil, preferably at least one non-ionic surfactant from the group of compounds with the INCI names Steareth-30, Ceteareth-30, Oleth-30, Ceteareth-50, PEG-40 Hydrogenated Castor Oil and PEG-60 Hydrogenated Castor Oil, in particular PEG-40 Hydrogenated Castor Oil.

14. The cosmetic product according to any one of the preceding points, exemplified in that product contains, in relation to its total weight, less than 2.0 wt. %, preferably less than 1.0 wt. %, particularly preferably less than 0.1 wt. %, and in particular no anionic and amphoteric surfactant.

15. The cosmetic product according to any one of the preceding points, exemplified in that the cosmetic product also contains, in relation to its total weight, from about 0.1 to about 2.0 wt. %, preferably from about 0.15 to about 1.5 wt. %, and in particular from about 0.2 to about 1.0 wt. % of chitosan or chitosan derivative, preferably a neutralisation product of chitosan with at least one acid.

16. The cosmetic product according to any one of the preceding points, exemplified in that the cosmetic product contains, in relation to its total weight, from about 50 to about 99 wt. %, preferably from about 55 to about 97 wt. %, particularly preferably from about 60 to about 95 wt. %, and in particular from about 70 to about 92 wt. % of water or a water-alcohol mixture.

17. The cosmetic product according to any one of the preceding points, exemplified in that the cosmetic product contains, in relation to its total weight, from about 1 to about 15 wt. %, particularly preferably from about 2 to about 12.5 wt. %, and in particular from about 3 to about 10 wt. % of at least one propellant, preferably propane and/or butane.

18. Use of a cosmetic product according to any one of the preceding points to
    temporarily reshape keratin fibers
    improve the hairstyle hold
    increase the hair volume
    improve the manageability, in particular the combability.

19. Use of a cosmetic product according to one of the preceding points to reduce damage to the hair, in particular hair breakage.

20. A method for temporarily shaping keratin fibers, in particular human hair, in which a cosmetic product according to any one of the preceding points is applied to the keratin fibers.

A first subject of this application is constituted by cosmetic products for temporarily reshaping keratin-containing fibers, in particular human hair, containing, in a cosmetic carrier, in relation to the total weight thereof, a) from about 0.01 to about 10 wt. % of at least one (meth)acrylamidopropyltrimethylammonium salt homo- or copolymer; and b) from about 0.1 to about 10 wt. % of at least one non-ionic, anionic and/or amphoteric film-forming polymer.

The cosmetic products as contemplated herein contain their active agents in a cosmetic carrier, preferably in an aqueous cosmetic carrier, alcoholic cosmetic carrier, or an aqueous-alcoholic cosmetic carrier. For the purpose of temporary hair reshaping, such carriers are, for example, lotions, water-in-oil emulsions, oil-in-water emulsions, creams, gels, mousses, pomades, waxes or other preparations suitable for use on the hair.

It is preferred as contemplated herein that the cosmetic carrier is an aqueous cosmetic carrier or an aqueous-alcoholic cosmetic carrier. It is also preferred as contemplated herein that the cosmetic carrier of the product as contemplated herein contains water, such that the product contains at least 50 wt. % water, in relation to the total weight of said product.

Aqueous-alcoholic carriers, in the sense of the present disclosure, are understood to mean aqueous compositions that contain water and, for example, $C_1$-$C_4$ alcohol, in particular ethanol or isopropanol, methoxybutanol, benzyl alcohol, ethyldiglycol, 1,2-propylene glycol or 1,3-propylene glycol.

A preferred embodiment of the present disclosure is exemplified in that the cosmetic products contain, in relation to their total weight, from about 50 to about 99 wt. %, preferably from about 55 to about 97 wt. %, particularly preferably from about 60 to about 95 wt. %, and in particular from about 80 to about 92 wt. % of water or a water-alcohol mixture.

A first essential constituent of cosmetic products as contemplated herein is the (meth)acrylamidopropyltrimethylammonium salt homo- or copolymer. The addition of this cationic polymer to the cosmetic products improves not only the nourishing effect thereof, for example in relation to the combability of the hair, but also surprisingly improves the holding effect of the product, in other words it intensifies the cosmetic effect of the non-ionic, anionic or amphoteric film-forming polymer b).

(Meth)acrylamidopropyltrimethylammonium salt homopolymers and equally (meth)acrylamidopropyltrimethylammonium salt copolymers can be used as essential constituent a).

It has proven to be cosmetically advantageous if, as (meth)acrylamidopropyltrimethylammonium salt homopolymer a), a (3-acrylamidopropyl)trimethylammonium salt homopolymer, preferably a (3-acrylamidopropyl)trimethylammonium chloride homopolymer is used. Corresponding cosmetic products are therefore preferred as contemplated herein.

In a second group of preferred cosmetic products, (3-methacrylamidopropyl)trimethylammonium salt homopolymer, preferably (3-methacrylamidopropyl)trimethylammonium chloride homopolymer is used as (meth) acrylamidopropyltrimethylammonium salt homopolymer.

Of course, the cosmetic products as contemplated herein can also contain mixtures of (3-acrylamidopropyl)trimethylammonium salt homopolymer and (3-methacrylamidopropyl)trimethylammonium salt homopolymer, in particular mixtures of (3-acrylamidopropyl)trimethylammonium chloride homopolymer and (3-methacrylamidopropyl)trimethylammonium chloride homopolymer.

Equally, mixtures of (3-acrylamidopropyl)trimethylammonium salt copolymer and (3-methacrylamidopropyl)trimethylammonium salt copolymer, in particular mixtures of (3-acrylamidopropyl)trimethylammonium chloride copolymer and (3-methacrylamidopropyl)trimethylammonium chloride copolymer can be used.

On account of its high positive charge density, the (meth) acrylamidopropyltrimethylammonium salt homo- or copolymer is able to effectively bind to the negatively charged surface of human hair.

Preferred (meth)acrylamidopropyltrimethylammonium salt homopolymers have a mean molecular mass M[r] of approximately 300,000.

Suitable (meth)acrylamidopropyltrimethylammonium salt homopolymers are freely commercially available for example from Ashland under the trade name N-DurHance A-1000 (INCI: Polyacrylamidopropyltrimonium Chloride).

In particular, the copolymers of (meth)acrylamidopropyltrimethylammonium salt with non-ionic monomers are suitable as (meth)acrylamidopropyltrimethylammonium salt copolymers. Particularly preferred non-ionic monomers are the acrylamides.

Suitable (meth)acrylamidopropyltrimethylammonium salt copolymers are freely commercially available for example from Ashland under the trade name N-Hance SP-100 (INCI: Acrylamidopropyl trimonium chloride/acrylamide copolymer).

The proportion by weight of the (meth)acrylamidopropyltrimethylammonium salt homo- or copolymer, preferably of the (meth)acrylamidopropyltrimethylammonium salt homopolymer in the total weight of the cosmetic product is preferably from about 0.02 to about 8.0 wt. %, preferably from about 0.05 to about 6.0 wt. %, and in particular from about 0.1 to about 3.0 wt. %.

The products as contemplated herein contain, as a second essential constituent, at least one non-ionic, anionic and/or amphoteric film-forming polymer. The film-forming polymer is different from the (meth)acrylamidopropyltrimethylammonium salt homo- or copolymer a). The proportion by weight of the film-forming polymer b) in the total weight of the cosmetic product is preferably from about 0.2 to about 9.0 wt. %, preferably from about 0.25 to about 8.0 wt. %, and in particular from about 0.3 to about 7.0 wt. %.

Examples of conventional film-forming polymers are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-acrylates/Acrylamide Copolymer, Aminoethylpropanediol-AMPD-acrylates/Diacetoneacrylamide Copolymer, Ammonium VA/Acrylates Copolymer, AMPD-acrylates/Diacetoneacrylamide Copolymer, AMP-acrylates/Allyl Methacrylate Copolymer, AMP-acrylates/C1-18 Alkyl Acrylates/C1-8 Alkyl Acrylamide Copolymer, AMP-acrylates/Diacetoneacrylamide Copolymer, AMP-acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/

Acrylates Copolymer, Octyl-acrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polysilicone-9, Polyurethane-1, Polyurethane-6, Polyurethane-10. Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethyl siloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

A group of film-forming polymers b) used with preference in the cosmetic product is constituted by the non-ionic polymers.

The group of non-ionic film-forming non-ionic polymers that are particularly preferred on account of their cosmetic effect and application properties in turn includes the vinylpyrrolidone homo- and copolymers.

Film-forming non-ionic film-forming polymers used with particular preference are:
polyvinylpyrrolidones, as are sold for example under the name Luviskol® (BASF),
vinylpyrrolidone/vinyl ester copolymers, as sold for example under the trade name Luviskol® (BASF).

On account of their cosmetic effect in combination with (meth)acrylamidopropyltrimethylammonium salt homopolymer, the polyvinylpyrrolidones (INCI name: PVP) and the vinylpyrrolidone/vinyl acetate copolymers (INCI name VP/VA Copolymer) are preferred and can be used individually or in combination.

In a first embodiment of preferred cosmetic products, these contain, in relation to their total weight, from about 0.1 to about 6.0 wt. %, preferably from about 0.2 to about 5.0 wt. %, and in particular from about 0.5 to about 4.0 wt. % of vinylpyrrolidone homopolymer.

In a second embodiment of preferred cosmetic products, these contain, in relation to their total weight, from about 0.1 to about 6.0 wt. %, preferably from about 0.2 to about 5.0 wt. %, and in particular from about 0.5 to about 4.0 wt. % of vinyl acetate/vinylpyrrolidone copolymer.

In a third embodiment of preferred cosmetic products, these contain, in relation to their total weight, from about 0.1 to about 4.0 wt. %, preferably from about 0.1 to about 2.0 wt. %, and in particular from about 0.1 to about 1.0 wt. % of vinylpyrrolidone homopolymer and also from about 0.1 to about 6.0 wt. %, preferably from about 0.2 to about 5.0 wt. %, and in particular from about 0.5 to about 4.0 wt. % of vinyl acetate/vinylpyrrolidone copolymer.

Besides the two aforementioned constituents, the cosmetic products as contemplated herein can contain further active agents or auxiliaries, wherein in particular active agents or auxiliaries that improve the producibility, application and/or cosmetic effect of these products are preferred.

A first group of preferred active agents or auxiliaries is constituted by the cationic nourishing substances. Preferred cosmetic products also contain, in relation to their total weight, from about 0.1 to about 6.0 wt. %, preferably from about 0.2 to about 5.0 wt. %, preferably from about 0.3 to about 4.0 wt. %, and in particular from about 0.4 to about 3.0 wt. % of at least one cationic nourishing active agent different from the (meth)acrylamidopropyltrimethylammonium salt homopolymer.

Particularly preferred cationic nourishing active agents are selected from the group of cationic surfactants, in particular from the group of quaternary ammonium compounds, esterquats and amidoamines. Cationic surfactants from the group of quaternary ammonium compounds are particularly preferred.

Preferred quaternary ammonium compounds are ammonium halides, in particular chlorides and borimdes, such as alkyltrimethylammonium chlorides, dialkyldimethylammonium chlorides, and trialkylmethylammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known by the INCI names Quaternium-27 and Quaternium-83. The long alkyl chains of the above-mentioned surfactants preferably have 10 to 18 carbon atoms. Cosmetic products that are very particularly preferred as contemplated herein contain, in relation to their total weight from about 0.05 to about 3.0 wt. %, particularly preferably from about 0.1 to about 2.0 wt. %, and in particular from about 0.1 to about 1.0 wt. % ($C_{12}$ to $C_{18}$) alkyltrimethylammonium salt(s).

A second group of particularly preferred cationic nourishing active agents is formed by the cationic polymers different from the (meth)acrylamidopropyltrimethylammonium salt homo- or copolymer. In order to improve the hair-cosmetic properties, in particular the nourishing and styling properties, cationic polymers with the INCI names Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polyquaternium-68 and Polyquaternium-69 can be used, in particular.

The preferred cationic polymers different from the (meth) acrylamidopropyltrimethylammonium salt homo- or copolymer include, in particular the cationic cellulose derivatives, in particular those that are formed from a reaction of hydroxyethylcellulose with a dimethyldiallylammonium reactant (in particular dimethyldiallylammonium chloride) optionally in the presence of further reactants. From these cationic celluloses, those that are particularly preferred are the cationic celluloses with the INCI name Polyquaternium-4. Corresponding celluloses are sold for example under the names Celquat® H 100 and Celquat® L 200 by the company National Starch;

the copolymers of vinylpyrrolidone with quaternised derivatives of dialkylaminoalkylacrylate and -methacrylate, in particular copolymers of vinylpyrrolidone and dimethylaminoethylmethacrylate quaternised with diethyl sulfate (INCI name: Polyquaternium-11). Corresponding polymers are obtainable for example under the trade names Gafquat® 440, Gafquat® 734 and Gafquat® 755 N (ISP);

copolymers of methacryloylaminopropyllauryldimethylammonium chloride with vinylpyrrolidone and dimethylaminopropylmethacrylamide (INCI name: Polyquaternium-55), which for example are obtainable from the company ISP under the trade names Styleze® W-10 or Styleze® W-20;

copolymers of N-vinylpyrrolidone, N-vinylcaprolactam, N-(3-dimethylaminopropyl)methacrylamide and 3-(methacryloylamino)propyl-lauryl-dimethylammonium chloride (INCI name: Polyquaternium-69), which for example are sold under the trade name AquaStyle® 300 (28-32 wt. % active substance in ethanol-water mixture, molecular weight 350,000) by the company ISP.

N-methylvinylimidazol/vinylpyrrolidone copolymers (INCI name: Polyquaternium-16), which for example are sold by the company BASF under the trade names Luviquat® Style, Luviquat® FC 370, Luviquat® FC 550, Luviquat® FC 905 and Luviquat® HM 552.

N-methylvinylimidazol/vinylpyrrolidone copolymers (INCI name: Polyquaternium-16), which are sold for example by BASF under the trade names Luviquat® Style, Luviquat® FC 370, Luviquat® FC 550, Luviquat® FC 905 and Luviquat® HM 552.

Due to their above-average styling properties, cosmetic products are preferred in particular that contain both a non-ionic polymer and a cationic polymer different from the (meth)acrylamidopropyltrimethylammonium salt homo- or copolymer.

In order to improve the producibility, application and cosmetic effect, the cosmetic products preferably contain a non-ionic surfactant, wherein particularly preferred cosmetic products contain, in relation to their total weight, from about 0.05 to about 2.0 wt. %, preferably from about 0.1 to about 1.0 wt. %, and in particular from about 0.1 to about 0.5 wt. % of at least one non-ionic surfactant, preferably at least one non-ionic surfactant from the group of addition products of 30 to 60 mol ethylene oxide with castor oil and hardened castor oil, preferably at least one non-ionic surfactant from the group of compounds with the INCI names Steareth-30, Ceteareth-30, Oleth-30, Ceteareth-50, PEG-40 Hydrogenated Castor Oil and PEG-60 Hydrogenated Castor Oil, in particular PEG-40 Hydrogenated Castor Oil.

Preferred non-ionic surfactants are PEG derivatives of hydrogenated castor oil which are obtainable for example under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil or PEG-60 Hydrogenated Castor Oil. Non-ionic surfactants selected from the group of PEG derivatives of hydrogenated castor oil, particularly preferably from the group of PEG-40 Hydrogenated Castor Oil and PEG-60 Hydrogenated Castor Oil, in particular PEG-40 Hydrogenated Castor Oil, are particularly preferably contained as contemplated herein.

For the cosmetic effect, formulation and application, it has proven to be particularly advantageous if the cosmetic products as contemplated herein contain, in relation to their total weight, less than 2.0 wt. %, preferably less than 1.0 wt. %, particularly preferably less than 0.1 wt. %, and in particular no anionic and amphoteric surfactant.

The cosmetic effect of products as contemplated herein can be further increased by the addition of chitosan or chitosan derivatives. The cosmetic products contain, in relation to their total weight, preferably from about 0.1 to about 2.0 wt. %, preferably from about 0.15 to about 1.5 wt. %, and in particular from about 0.2 to about 1.0 wt. % of chitosan or chitosan derivative, preferably a neutralisation product of chitosan with at least one acid.

Chitosans are biopolymers and belong to the group of hydrocolloids. Considered chemically, they are partially deacetylated chitins of different molecular weight. In order to produce chitosans, chitin is used as a starting point, preferably the shell residues of crustaceans, which are available in large quantities as inexpensive raw materials. The chitin is usually first deprotonated here by addition of bases, is demineralised by addition of mineral acids, and lastly is deacetylated by addition of strong bases, wherein the molecular weights can be distributed over a broad spectrum. Types that have a mean molecular weight (weight average) of from about 800,000 to about 1,200,000 daltons, a Brookfield viscosity (1 wt. % in glycolic acid) below 5,000 mPas, a degree of deacetylation ranging from about 80 to about 88%, and an ash content of less than 0.3 wt. % are preferably used.

Besides the chitosans as typical biopolymers, cationically derived chitosans (such as quaternisation products) or alkoxylated chitosans are also potential derivatives of chitosan.

Products that are preferred as contemplated herein contain, as chitosan, at least one neutralisation product of chitosan with at least one organic carboxylic acid, such as in particular formic acid, acetic acid, citric acid, lactic acid, pyrrolidone carboxylic acid, tartaric acid, glycolic acid, nicotinic acid, hydroxyisobutyric acid, hydroxyisovaleric acid, or mixtures of these acids. Here, it is preferred as contemplated herein to select the organic carboxylic acid from lactic acid, formic acid, pyrrolidone carboxylic acid, nicotinic acid, hydroxyisobutyric acid, hydroxyisovaleric acid or mixtures of these acids. This neutralization product can be produced for example in an aqueous medium by addition of chitosan and the corresponding organic carboxylic acid.

Suitable chitosans are freely commercially available, for example under the trade names Hydagen® CMF (1 wt. % active substance in aqueous solution with 0.4 wt. % glycolic acid, molecular weight from about 500,000 to about 5,000,000 g/mol, Cognis), Hydagen® HCMF (Chitosan 80% deacetylated, molecular weight 50,000 to 1,000,000 g/mol, Cognis), Kytamer® PC (80 wt. % active substance of chitosan pyrrolidone carboxylate (INCI name: Chitosan PCA), Amerchol) and Chitolam® NB/101.

Additional nourishing substances can be cited in particular as further suitable active agents or auxiliaries.

A first group of preferred nourishing components is formed by silicones, in particular the
- alkoxylated dimethicones, preferably from the group of ethoxylated/propoxylated dimethicones;
- aminofunctional silicones.

The group of alkoxylated dimethicones includes, for example,
- ethoxylated dimethicones with the INCI name PEG-x Dimethicone with x=2 to about 20, preferably from about 3 to about 17 and in particular 11 or 12;
- the ethoxylated dimethicones with the INCI name Bis-PEG-y Dimethicone with x=3 to about 25, preferably from about 4 to about 20;
- the ethoxylated/propoxylated dimethicones with the INCI name PEG/PPG a/b Dimethicone, wherein a and b independently of one another stand for numbers from about 2 to about 30, preferably from about 12 to about 24 and in particular from about 14 to about 20;
- the ethoxylated/propoxylated dimethicone with the INCI name Bis-PEG/PPG-c/d Dimethicone, wherein c and d independently of one another stand for numbers from about 10 to about 25, preferably from about 14 to about 20 and in particular from about 14 to about 16;
- the ethoxylated/propoxylated dimethicones with the INCI name Bis-PEG/PPG-e/f PEG/PPG g/h Dimethicone, wherein e, f, g and h independently of one another stand for numbers from about 10 to about 20, preferably from about 14 to about 18 and in particular 16.

As nourishing substance, the product can also contain at least one protein hydrolysate and/or a derivative thereof, for example. Protein hydrolysates are product mixtures which are obtained by acid-catalyzed, base-catalyzed or enzymatically catalyzed breakdown of proteins (albumins). The term "protein hydrolysates" is understood as contemplated herein to also mean total hydrolysates and also individual amino acids and derivatives thereof as well as mixtures of different amino acids. The molecular weight of the protein hydrolysates usable as contemplated herein lies between about 75, the molecular weight for glycine, and about 200,000, and the molecular weight is preferably from about 75 to about 50,000, and very particularly preferably from about 75 to about 20,000 daltons.

As nourishing substance, the product as contemplated herein can also contain at least one vitamin, a provitamin, a vitamin precursor and/or one of the derivatives thereof. Here, vitamins, provitamins and vitamin precursors that are usually assigned to the groups A, B, C, E, F and H are preferred as contemplated herein.

Further nourishing substances are panthenol, caffeine, nicotinamide and sorbitol.

As nourishing ingredient, the products as contemplated herein can also contain at least one plant extract, but also monosaccharides or oligosaccharides and/or lipids.

The composition of some particularly preferred cosmetic products as contemplated herein can be deduced from the following tables (values specified in wt. % in relation to the total weight of the cosmetic product, unless specified otherwise).

|  | Formula 1 | Formula 2 | Formula 3 | Formula 4 |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 6 | Formula 7 | Formula 8 | Formula 9 |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 11 | Formula 12 | Formula 13 | Formula 14 |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 16 | Formula 17 | Formula 18 | Formula 19 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 21 | Formula 22 | Formula 23 | Formula 24 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 26 | Formula 27 | Formula 28 | Formula 29 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| further ingredients | to 100 | to 100 | to 100 | to 100 |

|  | Formula 31 | Formula 32 | Formula 33 | Formula 34 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 36 | Formula 37 | Formula 38 | Formula 39 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 41 | Formula 42 | Formula 43 | Formula 44 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 46 | Formula 47 | Formula 48 | Formula 49 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 51 | Formula 52 | Formula 53 | Formula 54 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 56 | Formula 57 | Formula 58 | Formula 59 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| further ingredients | to 100 | to 100 | to 100 | to 100 |

|  | Formula 61 | Formula 62 | Formula 63 | Formula 64 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

* polymer different from the (meth)acrylamidopropyltrimethylammonium salt homo- or copolymer

|  | Formula 66 | Formula 67 | Formula 68 | Formula 69 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

* polymer different from the (meth)acrylamidopropyltrimethylammonium salt homo- or copolymer

|  | Formula 70 | Formula 71 | Formula 72 | Formula 73 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

* polymer different from the acrylamidopropyltrimethylammonium salt homo- or copolymer

|  | Formula 76 | Formula 77 | Formula 78 | Formula 79 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 81 | Formula 82 | Formula 83 | Formula 84 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 86 | Formula 87 | Formula 88 | Formula 89 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |

|  | Formula 86 | Formula 87 | Formula 88 | Formula 89 |
|---|---|---|---|---|
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 91 | Formula 92 | Formula 93 | Formula 94 |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

|  | Formula 96 | Formula 97 | Formula 98 | Formula 99 |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

|  | Formula 101 | Formula 102 | Formula 103 | Formula 104 |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

|  | Formula 106 | Formula 107 | Formula 108 | Formula 109 |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 111 | Formula 112 | Formula 113 | Formula 114 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 116 | Formula 117 | Formula 118 | Formula 119 |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| further ingredients | to 100 | to 100 | to 100 | to 100 |

|  | Formula 121 | Formula 122 | Formula 123 | Formula 124 |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

|  | Formula 126 | Formula 127 | Formula 128 | Formula 129 |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

|  | Formula 131 | Formula 132 | Formula 133 | Formula 134 |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| further ingredients | to 100 | to 100 | to 100 | to 100 |

The cosmetic products as contemplated herein are provided in the form of a mousse in accordance with a further preferred embodiment. For this purpose, the products as contemplated herein are provided in a dispensing device which is either a compressed gas container filled additionally with a propellant (aerosol container) or a non-aerosol container. The compressed gas container, with the aid of which a product is dispensed via a valve by employing the internal gas pressure of the container, is referred to, by definition, as an "aerosol container". A "non-aerosol container", in contrast to the aerosol definition, defines a container under normal pressure, with the aid of which a product is dispensed by a pumping or squeezing system by employing mechanical action. The cosmetic products as contemplated herein, within this embodiment, are particularly preferably present in the form of an aerosol mousse in an aerosol container. The product as contemplated herein therefore preferably additionally contains at least one propellant.

Products as contemplated herein that are present in the form of an aerosol product can be produced in the conventional way. Generally, all constituents of the product as contemplated herein with the exception of the propellant are filled into a suitable, pressure-resistant container. This is then closed by a valve. Lastly, the desired quantity of propellant is added by employing conventional techniques.

In the embodiment as aerosol mousse, propellants that are suitable as contemplated herein are selected for example from $N_2O$, dimethyl ether, $CO_2$, air, alkanes with from about 3 to about 5 carbon atoms, such as propane, n-butane, iso-butane, n-pentane and iso-pentane, and mixtures thereof.

In accordance with the embodiment of an aerosol mousse, the aforementioned alkanes, mixtures of said alkanes, or mixtures of the aforementioned alkanes with dimethyl ether are used as the sole propellant. However, the present disclosure also expressly comprises the co-use of propellants of the chlorofluorocarbon type, but in particular of the fluorinated hydrocarbon type. Dimethyl ether, propane, n-butane, iso-butane and mixtures thereof are preferred. Mixtures of propane and butane as the sole propellant used in a ratio by weight of propane to butane of from about 70 to about 30 to from about 15 to about 85 are very particularly preferred. As contemplated herein, butane is understood to mean n-butane, iso-butane and mixtures of n-butane and iso-butane.

The propellants are used in the cosmetic products as contemplated herein preferably in an amount of from about 1 to about 15 wt. %, particularly preferably from about 2 to about 12.5 wt. %, and in particular from about 3 to about 10 wt. %—in relation to the weight of the total product—wherein propane, butane and propane/butane mixtures are preferred.

The compositions of further preferred cosmetic compositions can be deduced from the following tables (values specified in wt. % in relation to the total weight of the composition, unless specified otherwise).

|  | Formula 1a | Formula 2a | Formula 3a | Formula 4a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 6a | Formula 7a | Formula 8a | Formula 9a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |

-continued

|  | Formula 6a | Formula 7a | Formula 8a | Formula 9a |
|---|---|---|---|---|
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 11a | Formula 12a | Formula 13a | Formula 14a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic, anionic and/or amphoteric film-forming polymer | 0.1 to 10 | 0.2 to 9.0 | 0.25 to 8.0 | 0.3 to 7.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 16a | Formula 17a | Formula 18a | Formula 19a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 21a | Formula 22a | Formula 23a | Formula 24a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 26a | Formula 27a | Formula 28a | Formula 29a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 31a | Formula 32a | Formula 33a | Formula 34a |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 36a | Formula 37a | Formula 38a | Formula 39a |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 41a | Formula 42a | Formula 43a | Formula 44a |
| --- | --- | --- | --- | --- |
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 46a | Formula 47a | Formula 48a | Formula 49a |
| --- | --- | --- | --- | --- |
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 51a | Formula 52a | Formula 53a | Formula 54a |
| --- | --- | --- | --- | --- |
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 56a | Formula 57a | Formula 58a | Formula 59a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| polyvinylpyrrolidone | 0.1 to 10 | 0.1 to 6.0 | 0.2 to 5.0 | 0.5 to 4.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 61a | Formula 62a | Formula 63a | Formula 64a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

\* polymer different from the (meth)acrylamidopropyltrimethylammonium salt homo- or copolymer

|  | Formula 66a | Formula 67a | Formula 68a | Formula 69a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

\* polymer different from the methacrylamidopropyltrimethylammonium salt homo- or copolymer

|  | Formula 70a | Formula 71a | Formula 72a | Formula 73a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic polymer * | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

\* polymer different from the acrylamidopropyltrimethylammonium salt homo- or copolymer

|  | Formula 76a | Formula 77a | Formula 78a | Formula 79a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |

-continued

|  | Formula 76a | Formula 77a | Formula 78a | Formula 79a |
|---|---|---|---|---|
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

10

|  | Formula 81a | Formula 82a | Formula 83a | Formula 84a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 86a | Formula 87a | Formula 88a | Formula 89a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 91a | Formula 92a | Formula 93a | Formula 94a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 96a | Formula 97a | Formula 98a | Formula 99a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |

-continued

|  | Formula 96a | Formula 97a | Formula 98a | Formula 99a |
|---|---|---|---|---|
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 101a | Formula 102a | Formula 103a | Formula 104a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| non-ionic polymer | 0.1 to 10 | 0.2 to 9.0 | 0.25 to 8.0 | 0.3 to 7.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 106a | Formula 107a | Formula 108a | Formula 109a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 111a | Formula 112a | Formula 113a | Formula 114a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 116a | Formula 117a | Formula 118a | Formula 119a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |

-continued

|  | Formula 116a | Formula 117a | Formula 118a | Formula 119a |
|---|---|---|---|---|
| Polyquaternium-4 and/or Polyquaternium-11 | 0.1 to 6.0 | 0.2 to 5.0 | 0.3 to 4.0 | 0.4 to 3.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 121a | Formula 122a | Formula 123a | Formula 124a |
|---|---|---|---|---|
| (meth)acrylamidopropyltrimethylammonium salt homopolymer or (meth)acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 126a | Formula 127a | Formula 128a | Formula 129a |
|---|---|---|---|---|
| methacrylamidopropyltrimethylammonium salt homopolymer or methacrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

|  | Formula 131a | Formula 132a | Formula 133a | Formula 134a |
|---|---|---|---|---|
| acrylamidopropyltrimethylammonium salt homopolymer or acrylamidopropyltrimethylammonium salt copolymer | 0.01 to 10 | 0.02 to 8.0 | 0.05 to 6.0 | 0.1 to 3.0 |
| vinyl acetate/vinylpyrrolidone copolymer and/or polyvinylpyrrolidone | 0.1 to 10 | 0.2 to 9.0 | 0.25 to 8.0 | 0.3 to 7.0 |
| Polyquaternium-4 and/or Polyquaternium-11 | 0.1 to 6.0 | 0.2 to 5.0 | 0.3 to 4.0 | 0.4 to 3.0 |
| cationic surfactant | 0.01 to 4.0 | 0.05 to 3.0 | 0.1 to 2.0 | 0.1 to 1.0 |
| water | 50 to 99 | 55 to 97 | 60 to 95 | 70 to 92 |
| propellant, in particular propane/butane | 1.0 to 15 | 2.0 to 12.5 | 2.0 to 12.5 | 3.0 to 10 |
| further ingredients | to 100 | to 100 | to 100 | to 100 |

As mentioned in the introduction, the cosmetic compositions as contemplated herein are suitable in particular for
temporarily reshaping keratin fibers
improving the hairstyle hold
increasing the hair volume
improving the manageability, in particular the combability.

The corresponding uses of products as contemplated herein are therefore further subjects of this application.

A further subject of the application is the use of a cosmetic product as contemplated herein to reduce damage to hair, in particular hair breakage.

A last subject of the application is a method for temporarily shaping keratin fibers, in particular human hair, in which a cosmetic product as contemplated herein is applied to the keratin fibers.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for temporarily reshaping keratin-containing fibers comprising, in a cosmetic carrier, from about 0.01 to about 10 wt. % of a (meth)acrylamidopropyltrimethylammonium salt homo- or copolymer a), based on a total weight of the cosmetic product; and
from about 0.1 to about 10 wt. % of at least one non-ionic, anionic and/or amphoteric film-forming polymer b), wherein the at least one film-forming polymer comprises a vinylpyrrolidone/vinyl acetate copolymer.

2. The cosmetic product according to claim 1, wherein the proportion by weight of the (meth)acrylamidopropyltrimethylammonium salt homo- or copolymer a) in the total weight of the cosmetic product is from about 0.1 to about 3.0 wt. %, and
the proportion by weight of the vinylpyrrolidone/vinyl acetate copolymer is from about 0.3 to about 7.0 wt. %, based on the total weight of the cosmetic product.

3. The cosmetic product according to claim 1, wherein the (meth)acrylamidopropyltrimethylammonium salt homo- or copolymer is a (meth)acrylamidopropyltrimethylammonium salt homopolymer, wherein the proportion by weight of the (meth)acrylamidopropyltrimethylammonium salt homopolymer is from about 0.1 to about 3.0 wt. %, and wherein the proportion by weight of the vinylpyrrolidone/vinyl acetate copolymer is from about 0.3 to about 7.0 wt. %, wherein the wt. % are based on the total weight of the cosmetic product.

4. The cosmetic product according to claim 1, wherein:
the (meth)acrylamidopropyltrimethylammonium salt homo- or copolymer a) is present in the cosmetic composition in an amount of from about 0.1 to about 3.0 wt. %, based on the total weight of the cosmetic composition; and
the proportion by weight of the film-forming polymer b) in the total weight of the cosmetic product is from about 0.3 to about 7.0 wt. %, based on the total weight of the cosmetic product, wherein the film-forming polymer b) comprises a non-ionic film forming polymer, wherein the non-ionic film forming polymer consists of the vinylpyrrolidone/vinyl acetate copolymer, and wherein the non-ionic film forming polymer is present in the cosmetic product at from about 0.3 to about 7.0 weight percent, based on the total weight of the cosmetic product.

5. The cosmetic product according to claim 4, wherein the (meth)acrylamidopropyltrimethylammonium salt homo- or copolymer a) consists of a (meth)acrylamidopropyltrimethylammonium salt homopolymer.

6. The cosmetic product according to claim 1, wherein the cosmetic product comprises, in relation to its total weight, less than about 2.0 wt. % anionic and amphoteric surfactant.

7. The cosmetic product according to claim 1, wherein the cosmetic product comprises, in relation to its total weight, from about 50 to about 99 wt. % of water or a water-alcohol mixture.

8. The cosmetic product according to claim 1, wherein the cosmetic product comprises, in relation to its total weight, from about 1 to about 15 wt. % of at least one propellant.

9. A method for temporarily shaping keratin fibers, comprising:
applying a cosmetic product to the keratin fibers, wherein the cosmetic product comprises, in a cosmetic carrier:
from about 0.1 to about 3.0 wt. % of at least one (meth)acrylamidopropyltrimethylammonium salt homo- or copolymer a), based on a total weight of the cosmetic product; and
from about 0.3 to about 7.0 wt. % of at least one non-ionic, anionic and/or amphoteric film-forming polymer b), based on the total weight of the cosmetic product, and wherein the at least one film-forming polymer comprises a vinylpyrrolidone/vinyl acetate copolymer.

10. The cosmetic product according to claim 1, wherein the (meth)acrylamidopropyltrimethylammonium salt homo- or copolymer a) consists of (3-acrylamidopropyl)trimethylammonium salt homopolymer.

11. The cosmetic product according to claim 1, wherein the proportion by weight of the (meth)acrylamidopropyltrimethylammonium salt homo- or copolymer a), in relation to the total weight of the cosmetic product, is from about 0.05 to about 6.0 wt. %.

12. The cosmetic product according to claim 1, wherein the proportion by weight of the (meth)acrylamidopropyltrimethylammonium salt homo- or copolymer a), in relation to the total weight of the cosmetic product, is from about 0.1 to about 3.0 wt. %.

13. The cosmetic product according to claim 1, wherein the proportion by weight of the film-forming polymer b) in the total weight of the cosmetic product is from about 0.25 to about 8.0 wt. %.

14. The cosmetic product according to claim 1, wherein the proportion by weight of the film-forming polymer b) in the total weight of the cosmetic product is from about 0.3 to about 7.0 wt. %.

15. The cosmetic product according to claim 1, wherein the cosmetic product also comprises, in relation to its total weight, from about 0.2 to about 5.0 wt. % of at least one cationic nourishing active agent different from the (meth)acrylamidopropyltrimethylammonium salt homo- or copolymer a).

16. The cosmetic product according to claim 1, wherein the cosmetic product also comprises, in relation to its total weight, from about 0.3 to about 4.0 wt. % of at least one cationic nourishing active agent different from the (meth)acrylamidopropyltrimethylammonium salt homo- or copolymer a).

17. The cosmetic product according to claim 1, wherein the cosmetic product also comprises, in relation to its total weight, from about 0.4 to about 3.0 wt. % of at least one cationic nourishing active agent different from the (meth)acrylamidopropyltrimethylammonium salt homo- or copolymer a).

18. The cosmetic product according to claim 1, wherein the cosmetic product comprises, in relation to its total weight, less than about 0.1 wt. %, anionic and amphoteric surfactant.

19. The cosmetic product according to claim 1, wherein the cosmetic product comprises, in relation to its total weight, from about 60 to about 95 wt. % of water or a water-alcohol mixture.

20. The cosmetic product according to claim 1, wherein the cosmetic product comprises, in relation to its total weight, from about 70 to about 92 wt. % of water or a water-alcohol mixture.

\* \* \* \* \*